United States Patent [19]

Morinaga et al.

[11] Patent Number: 5,302,698
[45] Date of Patent: Apr. 12, 1994

[54] DNA CODING FOR PROTEIN BINDS TO ENHANCER OF α-FETOPROTEIN GENE

[75] Inventors: Tomonori Morinaga; Hisataka Yasuda, both of Shimotsuga; Kanji Higashio, Kawagoe, all of Japan; Taiki Tamaoki, Calgary, Canada

[73] Assignee: Snow Brand Milk Products Co., Ltd., Sapporo, Japan

[21] Appl. No.: 22,411

[22] PCT Filed: Apr. 27, 1990

[86] PCT No.: PCT/JP90/00557

§ 371 Date: Dec. 31, 1990

§ 102(e) Date: Dec. 31, 1990

[87] PCT Pub. No.: WO90/13655

PCT Pub. Date: Nov. 15, 1990

Related U.S. Application Data

[63] Continuation of Ser. No. 635,498, Dec. 31, 1990, abandoned.

[30] Foreign Application Priority Data

May 1, 1989 [JP] Japan ................................. 1-112519

[51] Int. Cl.$^5$ ...................... C07K 13/00; C12N 15/00; C12N 15/12
[52] U.S. Cl. ................................. 530/350; 435/172.3; 536/23.5
[58] Field of Search ............................ 435/69.1, 172.3; 530/350; 536/23.5

[56] References Cited

PUBLICATIONS

Morinaga et al., Proc. Natl. Acad. Sci. USA, vol. 80, pp. 4604–4608 (Aug. 1983).
Sakai et al., The Journal of Biological Chemistry, vol. 260, No. 8, pp. 5055, 5058–5060 (Apr. 25, 1985).
Sturm et al., Genes & Development, 2:1582–1599 (1988).
Clerc et al., Genes & Development, 2:1570–1581 (1988).
Okamoto et al., Cell, vol. 60, 461–472 (Feb. 9, 1990).
Frain et al., Cell, vol. 59, pp. 145–157 (Oct. 6, 1989).
Feuerman et al., Mol. and Cell. Biol., vol. 9, No. 10, pp. 4204–4212 (Oct. 1989).
Frain et al., Mol. and Cell. Biol., vol. 10, No. 3, pp. 991–999 (Mar. 1990).
Baumhueter et al., The EMBO Journal, vol. 7, No. 8, pp. 2485–2493 (1988).
Wang et al., "A specific α-Fetoprotein Gene . . . etc.", Biochemical and BioPhysical Research Communications, vol. 143, No. 1, 1987, pp. 110–115.
Watanabe et al., "Cell-specific enhancer activity . . . etc.", The Journal of Biological Chemistry, vol. 262, Issue of Apr. 5, pp. 4812–4818 (1987).
Sawaadaishi et al. (1988), Mol. Cell. Bio., vol. 8, pp. 5179–5187.
Singh et al. (1988), Cell, vo. 52, pp. 415–423.
Muller et al. (1988), Nature, vol. 336, pp. 544–551.
Courtois et al. (1988), Proc. Natl. Acad. Sci., vol. 85, pp. 7937–7941.
Scheidereit et al. (1988), Nature, vol. 336, pp. 551–557.

*Primary Examiner*—Richard A. Schwartz
*Assistant Examiner*—Nancy T. Vogel
*Attorney, Agent, or Firm*—Millen, White, Zelano, & Branigan

[57] ABSTRACT

This invention relates to a DNA coding for a protein that specifically binds to the enhancer of the α-fetoprotein gene and that promotes transcription of that α-fetoprotein gene. This DNA is useful, by applying recombinant DNA technology, for the construction of highly efficient gene expression system for the production of proteins having physiological activities in animal cells.

3 Claims, 10 Drawing Sheets

MetSerSerValAsnLeuAsnPheAspGlnThrLysLeuAspAsnAspAspCysSerSer
ValAsnThrAlaIleThrAspThrThrThrGlyAspGluGlyAsnAlaAspAsnAspSer
AlaThrGlyIleAlaThrGluThrLysSerSerSerAlaProAsnGluGlyLeuThrLys
AlaAlaMetMetAlaMetSerGluTyrGluAspArgLeuSerSerGlyLeuValSerPro
AlaProSerPheTyrSerLysGluTyrAspAsnGluGlyThrValAspTyrSerGluThr
SerSerLeuAlaAspProCysSerProSerProGlyAlaSerGlySerAlaGlyLysSer
GlyAspSerGlyAspArgProGlyGlnLysArgPheArgThrGlnMetThrAsnLeuGln
LeuLysValLeuLysSerCysPheAsnAspTyrArgThrProThrMetLeuGluCysGlu
ValLeuGlyAsnAspIleGlyLeuProLysArgValValGlnValTrpPheGlnAsnAla
ArgAlaLysGluLysLysSerLysLeuSerMetAlaLysHisPheGlyIleAsnGlnThr
SerTyrGluGlyProLysThrGluCysThrLeuCysGlyIleLysTyrSerAlaArgLeu
SerValArgAspHisIlePheSerGlnGlnHisIleSerLysValLysAspThrIleGly
SerGlnLeuAspLysGluLysGluTyrPheAspProAlaThrValArgGlnLeuMetAla
GlnGlnGluLeuAspArgIleLysLysAlaAsnGluValLeuGlyLeuAlaAlaGlnGln
GlnGlyMetPheAspAsnThrProLeuGlnAlaLeuAsnLeuProThrAlaTyrProAla
LeuGlnGlyIleProProValLeuLeuProGlyLeuAsnSerProSerLeuProGlyPhe
ThrProSerAsnThrAlaLeuThrSerProLysProAsnLeuMetGlyLeuProSerThr
ThrValProSerProGlyLeuProThrSerGlyLeuProAsnLysProSerSerAlaSer
LeuSerSer

FIG. 1

```
                                                                          1
                                                                          C
ATG TCC TCA GTT AAT CTA AAC TTT GAC CAA ACT AAG CTG GAC AAC GAT AAC AAC
ACA GCA ATC ACA GAT ACC ACA TCC TCT GCA GGA GAC GAG AAC GCA GAT GCA ATA
GCA ACT GAA ACC AAA TCC TCT TTG TCA TCT GGT CTG ACC TTG ACC CCG ATG GCA ATG
TCT GAG TAT CGG TTG TCA GTG GAT CGG AGT CCG AGT CCG AGC CTT TAT AGC AAG GAA
TAT GAC AAT GAA GGT ACA TCT GAC GGC AAA GCA GAT CCC GGG CAG TGC TCC CCG AGT
CCT GGT GCG AGT TCT GCA GGC AAT CTG AAG CGG TTT AAT GAC TAC AGG ACA CCC
CGC ACT CAA ATG GAA TGT GAG GTC CTG GGC AAT AGA AAG AGA AAG AGC CAG GTC TGG
ACT ATG GAA CTA GAA GCC CGG GCA AAA GAA ATT CCA CCA ATG GCC ATC AAG ATT CAG GTT ATA AAC
TTC CAG AAT GCC TAT GAG GAC CAT ATC TTT TCC CAA CAG CAG TTA AGC GAG CAG CAG CTG
CAA ACG CTA GAG GAG GCA AAA GAG CAA CAG CTA CAG TTT GTT TGT AAA ATC TCC ATC AGC GTT CGG CAG CAG
TCT GTA CGT GAC CAT ATC TTT TCC CAA CAG CAG TTA AGC GAG CAG CAG CTG
CTG GAC AAG GAG AAA GAA TAC TTT GAC CGT CAG GCA GCA CTG CCA GCC ACC GTA GCC ACC GCT CGG CAG CAG GGC ATT GCT CAA CAA GAG TTG
GAC CGG ATT AAA GCC GCC CTT ACA TCT CCT ACA GAG ATG TTT CAA CAG AAA CAG CTC GCA GCA CTG CCA GCC ATG TTT GAC AAC
ACC CCT CTT CAG GCC CTT AAC CCC TCC TTG CCA GGC TTT CCT GCT CCA CCA AAC CCT GCA ACT CCA AAC ACA CCG GGC TTT CCT CCT CCT TTT CCT CCT CCT GTG TTG
CTC CCG GGC CTC AAC AGC CCT CTG CCC CCC AGC ACA ACT CCA CCC TCC TTG CCT CCG CCT CTG CGG ACG TCT TTA
AAG CCG AAC TTG ATG GGT CCT CTG CCC CCC AGC ACA GTT CCT CCT CCT CCT CTC ACT CTC TCT GGA TTA

CCA AAT AAA CCG TCC TCA GCG TCG CTG AGC TCC C
                                         1091

```
            NlaIV                                      DdeI
             |                                          |
        AGGGAGCCTGATTAATAATTACACTAAGTCAA
        TCCCTCGGACTAATTATTAATGTGATTCAGTT
```

DNA CODING FOR PROTEIN BINDS TO ENHANCER OF α-FETOPROTEIN GENE

This application is a continuation of application Ser. No. 07/635,498, filed Dec. 31, 1990, now abandoned, which is based on international application PCT/JP90/00557 filed Apr. 27, 1990.

FIELD OF THE INVENTION

This invention relates to DNA coding for a protein which specifically binds to the enhancer of α-fetoprotein gene and promotes transcription of α-fetoprotein gene. Since the protein is involved in transcription, this DNA can be used for the construction of a highly efficient gene expression system utilizing animal cells.

BACKGROUND OF THE INVENTION

Expression of genetic information in eucaryotic cells is regulated at the levels of transcription into mRNA, mRNA processing, translation to protein and posttranslational processing. The regulation at the transcription level most strongly influences the expression of genetic information. A promoter which controls transcription is found on the 5' side of genes transcribed by RNA polymerase II and sometimes enhancers, which regulate promoter activity were also found. With the recent discovery of nuclear factors that recognize and bind to specific nucleotide sequences in the promoter and enhancers, it has become evident that the activities of promoter and also enhancers are mediated by the binding of these factors.

Of such factors, for example, studies on proteins which interact with TATA box, CAAT box, or GC box for the stimulation of transcription of RNA polymerase have been undertaken. Cloning of cDNA of CAAT-binding and GC-binding factors has already been accomplished.

Furthermore, factors that bind to enhancers have been investigated and cDNA clones of several transcription factors have been successfully isolated: for example, octamer transcription factor-2 (OTF-2), a B-cell lineage specific factor, that binds to immunoglobulin κ-chain gene enhancer [Michael et al.: Nature, 336, 544–551, (1988)] and OTF-1, which recognizes the same nucleotide sequence and was found ubiquitously in many tissues [R. A. Sturm, G. Das and W. Herr: Gene & Development, 2, 1852 (1988)].

In human α-fetoprotein gene, presence of an enhancer at 3.5 kb on the upstream of transcription start point has been confirmed. A factor that binds to this enhancer has been discovered and named AFP-1 [Sawadaishi et al.: Molecular and Cellular Biology, 8, 5179–5187 (1988)].

However, the structure and physiological properties of AFP-1, and on the gene which codes for AFP-1 has not been elucidated.

OUTLINE OF THE PRESENT INVENTION

The inventors have been investigating a nuclear factor that specifically interacts with a region, characterized by the TTAATAATTA (see ID NO:3) structure that exists in the enhancer of α-fetoprotein gene, and isolated a cDNA that encodes this factor. They determined the nucleotide sequence of the cDNA and deduced the amino acid sequence of the factor and accomplished the present invention.

Therefore, this invention offers a DNA, expressed by nucleotide sequence, that codes for a protein which binds to the enhancer of human α-fetoprotein gene.

Figure 1:
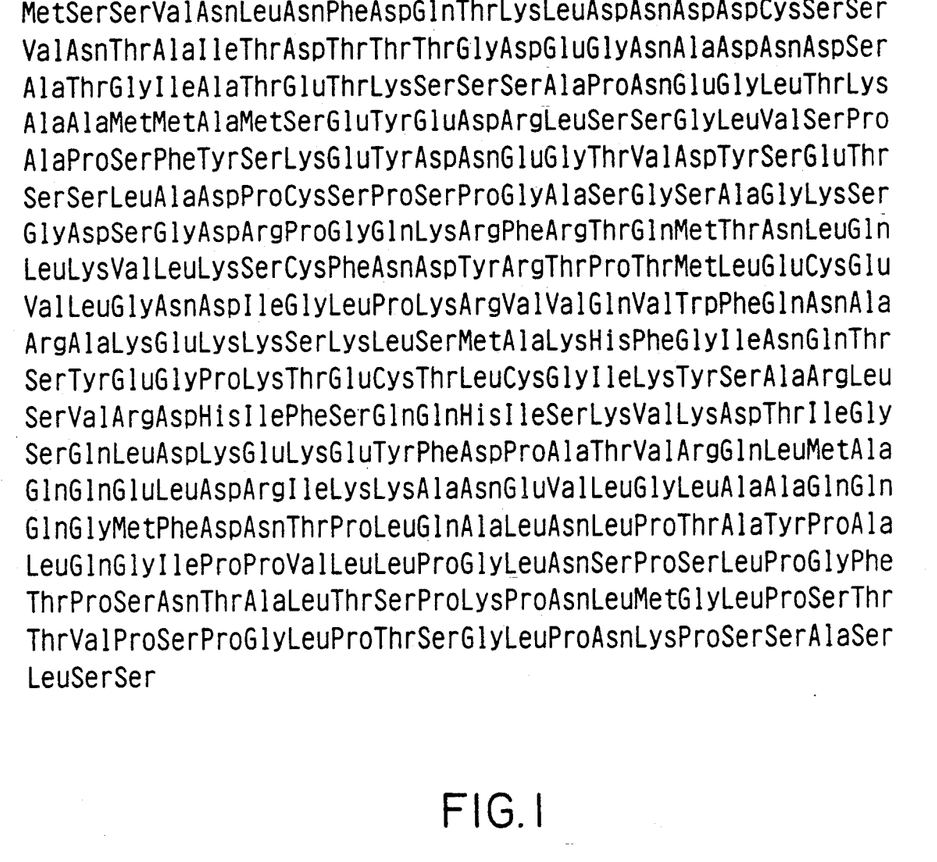
FIG. 1 shows the amino acid sequence (see ID NO:2) of the protein, which binds to the α-fetoprotein gene enhancer, encoded by the DNA (referred to as λ2cDNA) of this invention.
Figure 2:
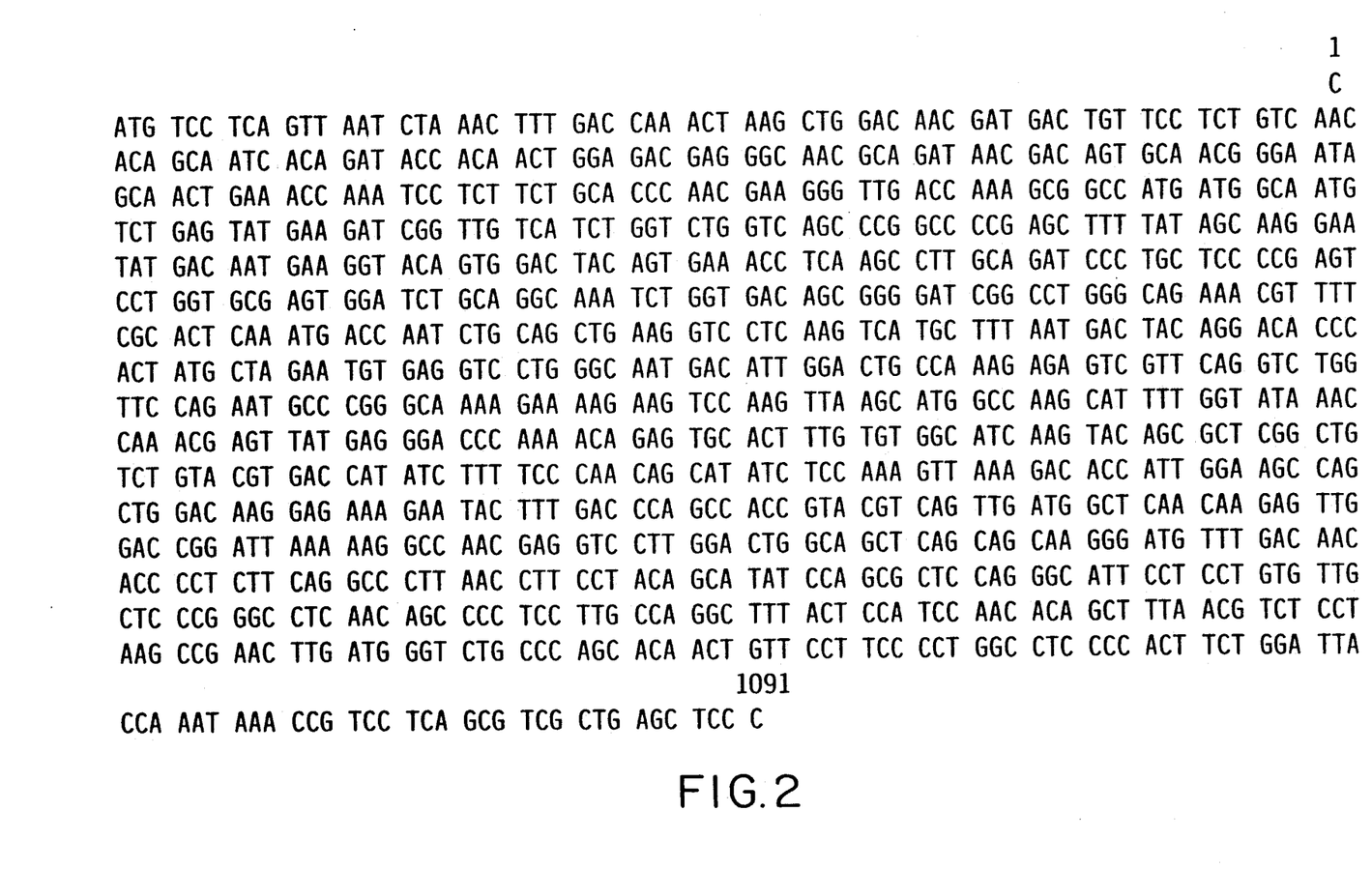
FIG. 2 shows the nucleotide sequence (see ID NO:1) of said DNA.

The nuclear factor which pertains to this invention and which specifically binds to the enhancer of α-fetoprotein gene, has the amino acid sequence given in FIG. 1, in its primary structure and present in cell nuclei, and can be extracted from α-fetoprotein-producing cells. Thus, it is possible to isolate the DNA defined by the nucleotide sequence given in FIG. 2, using cloning procedures starting with messenger RNA that is isolated from α-fetoprotein-producing cells derived from the liver.

BRIEF DESCRIPTION OF THE DRAWINGS

Hi and Ha signify the recognition sites of restriction enzymes HindIII and HaeIII, respectively.

FIG. 6, shows the result of DNase I foot print analysis using λ2 lysogen extract in the example. G+A represents a size marker prepared by the chemical cleavage of the probe DNA by the Maxam-Gilbert procedure; lane 1 signifies DNA extracted from the bands which is not retarded; lanes 2 and 3 show DNA extracted from the shifted bands (a) and (b), respectively.

[A] illustrates the pattern when 5' terminus at SmaI site is labeled (the indicated sequence in FIG. 6A is SEQ ID NO:6) labeled; [B] shows the pattern when 5' [B] shows the pattern when 5' terminus at HincII site is labeled; and [C] reveals the combination of the above two results (the upper sequence in FIG. 6C is SEQ ID NO:7; the lower sequence is SEQ ID NO:8).

PREFERRED EMBODIMENT OF THE INVENTION

The method for isolating the target DNA fragment pertaining to this invention is described below. The experimental procedure per se can be conducted by conventional methods.

One example of α-fetoprotein-producing cells is the human hepatoma cell line, HuH-7.

In this invention, the above mentioned α-fetoprotein-producing cells are cultured and the proliferated cells are collected, after which their RNA is extracted. The guanidinium isothiocyanate-cesium chloride method [J. M. Chirgwin et al.: Biochemistry, 18, 5294, (1979)] may be used for this purpose. Poly(A)RNA is separated by the standard procedure using oligo (dT) cellulose or the like.

Next, cDNA is synthesized using reverse transcriptase with poly(A)RNA, collected above, as a template. This cDNA is then converted into double-strand cDNA, which is packaged into λphase to make a recombinant phage.

For this purpose, commercial packaging systems, such as Packer Gene Packaging System (Promega Biotec) may be used.

The recombinant phage prepared as described above is then transfected with host enterobacter, e.g. *E. coli* Y1090 (r−) and subsequently plated on agarose plates to obtain a cDNA library. The target DNA, coding for the protein that binds to the α-fetoprotein gene enhancer, can be obtained by screening the library with the DNA fragment that contains the enhancer of α-fetoprotein gene.

The invention is explained in detail by the following example.

EXAMPLE

This example shows the preparation of DNA coding for a protein that binds to the enhancer of α-fetoprotein gene (hereinafter referred to as the enhancer) from poly(A)RNA isolated from HuH-7 cells derived from human hepatoma.

①  Growth of α-fetoprotein producing cells

Human hepatoma cell line, HuH-7, which produce α-fetoprotein was cultured under the following conditions. The cell line is available from Professor Jiro Sato, Pathology Division, Cancer Institute of Okayama University, Japan.

Conditions for culture

The medium used was RPMI-1640 medium added with 3% (w/w) lactalbumin hydrolysate (Gibco) or RPMI-1640 medium containing 5-10% (v/v) fetal calf serum. The medium was replaced as needed, and incubation was performed in an incubator (37° C.) filled with air containing 5% carbon dioxide.

②  Preparation of poly(A)RNA from the cells described above

Total RNA was extracted from $2 \times 10^8$ cells, adopting guanidinium isothiocyanate-cesium chloride method [Biochemistry, 18, 5294 (1979)], by the following procedure.

To the cells was added 20 ml solution composed of six M guanidine isothiocyanate, five mM sodium citrate, 0.1 M 2-mercaptoethanol and 0.5% sodium N-lauroyl sarcosinate, and the cells were homogenized at room temperature, then four g of cesium chloride was dissolved per 10 ml of this homogenate. In polyallomer centrifugal tubes were poured 2.5 ml solution composed of 5.7 M cesium chloride and 0.1 M EDTA (pH 7.5), over which 10 ml of the homogenate was layered. The layered mixture was then centrifuged at 34,000 rpm for 18 hours at 20° C. with Hitachi Ultracentrifuge Rotor RPS 40T (Hitachi Ltd.). The resultant sediment was dissolved in one ml solution composed of 10 mM Tris-HCl (pH 7.4), 5 mM of EDTA and 1% SDS. To this solution, an equal volume of a mixture of chloroform and n-butanol (4:1, v/v) was added, mixed well and centrifuged (16,000 g, 10 min.). To the obtained aqueous phase, one-tenth volume of 3 M sodium acetate (pH 5.5) and 2.5 volumes of ethanol were added and mixed well. The mixture was allowed to stand at −70° C. for more than two hours and centrifuged (16,000 g, 20 min.) to precipitate RNA. The precipitates were washed with 70% ethanol and then dried.

For the preparation of poly(A)RNA from the total RNA, affinity chromatography using oligo (dT) cellulose was employed as described below. Oligo (dT) cellulose (50 mg) was packed in a small column and equilibrated with a solution composed of 10 mM Tris-HCl (pH 7.5), 0.5 M NaCl, one mM of EDTA and 0.1% SDS. Then 390 μg of the total RNA dissolved in the same buffer was applied on the column. RNA that was not retained was washed out by the buffer, and the retained RNA was eluted with a solution composed of 10 mM Tris-HCl (pH 7.5), one mM EDTA and 0.05% SDS. To this eluate, 1/10 volume of 3 M sodium acetate (pH 5.5) and 2.5 volumes of ethanol were added, mixed, and the mixture was allowed to stand for more than two hours at −70° C.. The mixture was then centrifuged (12,000 g, 15 min.). The precipitates formed were washed with 70% ethanol, dried and dissolved in sterilized distilled water.

③  Synthesis of cDNA

A cDNA synthesizing kit (Pharmacia) was used for this purpose.

To the first-strand synthesis reaction mixture, 2.5 μg of poly(A)RNA and 0.4 μg of random primer, dp(N)$_6$ (Takara Shuzo Co., Ltd.) was added and then allowed to react according to the supplier's protocol. An EcoRI adapter was ligated to both ends of double-strand cDNA as directed by the protocol. From 2.5 μg poly(A)RNA, 2.3 μg of double-stranded cDNA was obtained.

④  Preparation of recombinant DNA and recombinant phage

Protoclone λgtll system (Promega) was used for the preparation of recombinant DNA using the double strand DNA describes above according to the protocol. The recombinant DNA thus obtained was transduced into recombinant phage using Packer, Gene Packaging System (Promega), and then transduced into *E. coli* Y1090 (r ). This recombinant phage was cultured on agarose plates to make a λgtll cDNA library. The complexity of this library was $3 \times 10^6$.

Figure 3:
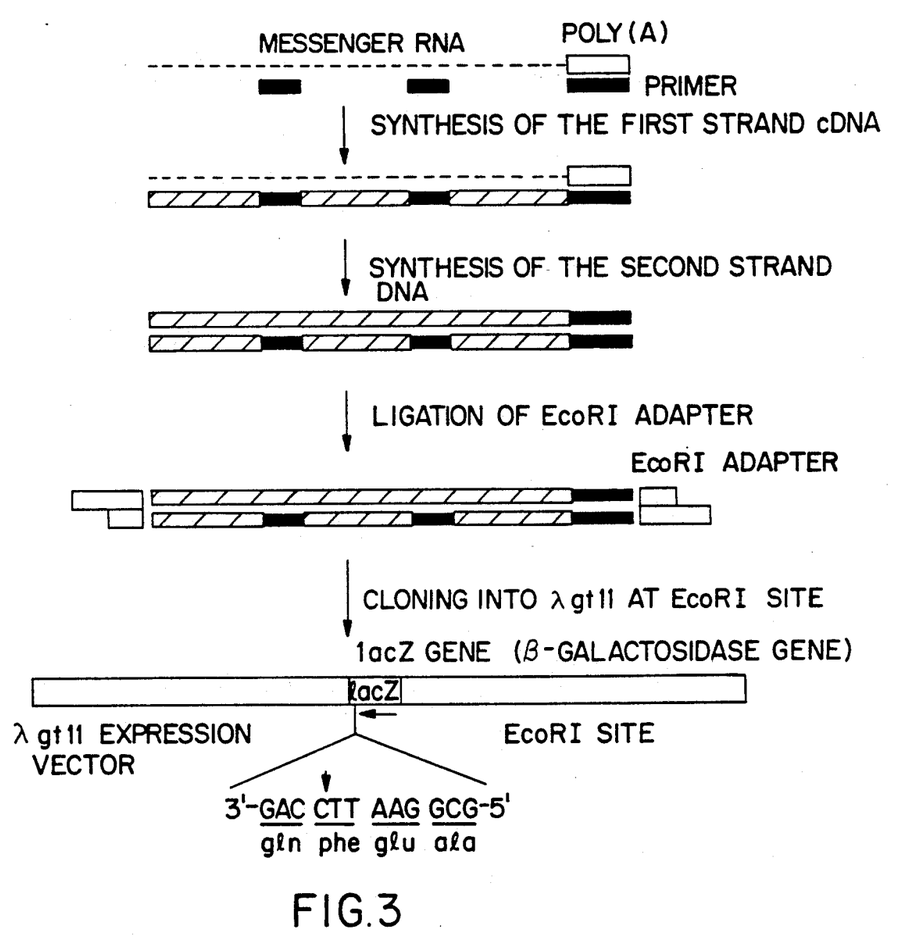
FIG. 3 describes briefly the procedure for obtaining cDNA starting with poly(A)RNA to introduce it into λgt11 expression vector in the example. The small arrows indicate the location in the DNA (SEQ ID NO:4) and amino acid (SEQ ID NO:5) sequences of the lacZ gene where the cDNA is to be inserted.

The processes of preparing cDNA and λgtll recombinant phage are shown in FIG. 3.

⑤  Preparation of probes and the method for the screening

Figure 4:
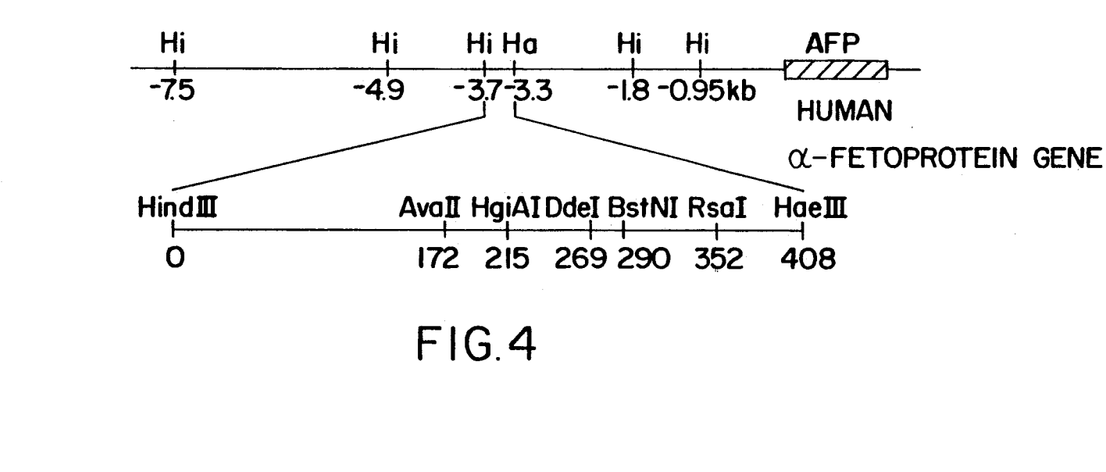
FIG. 4 illustrates a restriction enzyme map of the enhancer region located on the 5' side of human α-fetoprotein gene. The region from −3.3 kb to −3.7 kb is enlarged.

The above λgtll cDNA library was screened according to the known procedure [Cell, 52, 415, (1988)]. The probes for the screening were prepared from the DNA fragment of the human α-fetoprotein gene enhancer located upstream of the gene (see FIG. 4).

The DNA fragment having enhancer activity was isolated by digestion with restriction enzymes HgiAI and BstNI from the genomic DNA which had been extracted from HuH-7 cells and cloned into a λ phage vector, and its termini were filled with DNA polymerase I Klenow fragment. pUC18 plasmid was also treated with BamHI and the end was similarly treated. The two fragments were ligated using T4DNA ligase (Takara Shuzo Co., Ltd.) to give recombinant plasmid pAFE (HgiAI/BstNI)1.

The pAFE (HgiAI/BstNI) was subsequently digested using restriction enzymes XbaI and PstI, and deleted with exonuclease III and mung-bean nuclease (Takara Shuzo). Then the ends were filled in with DNA polymerase I Klenow fragment and the plasmid was recircularized by insertion of XhoI linker to the ends.

A clone which underwent deletion down to nine bases downstream from TTAATAAT sequence was screened from the deletion mutants obtained by the transduction of the plasmid into E. coli DH5 and designated as pAFE(HgiAI/XhoI)1. The pAFE(HgiAI/XhoI)1 was then hydrolyzed with restriction enzymes NlaIV and XhoI, and, a fragment containing enhancer was isolated by agarose gel electrophoresis. Ends of the (NlaIV/XhoI fragment was filled in with DNA polymerase I Klenow fragment, after which the fragments were self-ligated using T4 DNA ligase, and then the catenated DNA was cloned into HincII digested pUC18 plasmid using T4 ligase. E. coli DH5 α (BRL) was transformed with the obtained recombinant plasmid and an appropriate clone was screened from the recombinants on the basis of the number of NlaIV/XhoI fragment. Six NlaIV/XhoI fragments were catenated in the plasmid isolated from a clone at restriction site of HincII. This plasmid, named pAFE(NlaIV/XhoI)6, was cleaved with restriction enzymes SmaI and HincII (Takara Shuzo). Then the SmaI/HincII fragment containing the enhancer was isolated, labeled with T4 polynucleotide kinase and 5'[γ$^{32}$P] ATP and used as a probe for screening (referred to as the probe DNA).

According to the known method [Cell, 52, 415 (1988)], 3×10$^5$ plaques from the aforementioned library, which had been obtained by plating the recombinant phage, were screened to isolate clones that specifically interact with the probe. The single positive clone was named λ2. The agarose gel containing λ2 plaque was cut out of the plate and was suspended in a solution composed of 50 mM Tris-HCl (pH 7.5), 0.1 M NaCl, 8.1 mM MgSO$_4$ and 0.1% of gelatin to extract the phage. A drop of chloroform was added to the suspension and kept at 4° C.

⑥ Preparation of lysogen extracts

The phage prepared above was transduced into E. coli Y1089 according to a known method [DNA Cloning, Vol. 1, p. 49; Ed. by D. M. Grover, IRL Press (1985)] to prepare lysogens, from which an extract was prepared following the method described by Singh [Cell, 52, 415 (1988)]. As a control, λgtll phage having no cDNA was also transduced into E. coli Y1089, from which an extract was prepared by the similar method.

⑦ Gel Shift Assay

Gel shift assay was performed by a known method [Nature, 319, 154 (1988)] using the above mentioned lysogen extracts and DNA probe prepared from pAFE(HgiAI/BstNI) described in ⑤ as follows.

pAFE(HgiAI/BstNI)1 was cleaved with SamI and HincII to give an enhancer DNA fragment. A probe was prepared by labeling the SmaI/HincII fragment with 32p at the 5'-ends.

Figure 5:
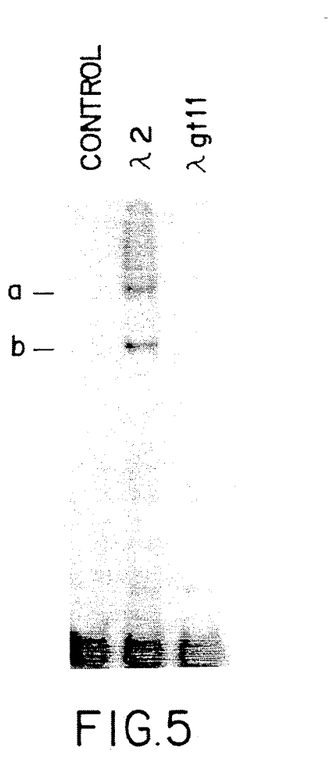
FIG. 5 displays the result of gel shift assay employing the extracts obtained from λ2 and λgt11 lysogens in the example. The control shows the pattern that occurred when the lysogen extract was eliminated. As shown in the figure, the two shifted bands (a and b) are visible only when the extract obtained from λ2 lysogen is used.

As shown in FIG. 5, two shifted bands (a and b) were detected in the extract made from λ2 lysogen, while such bands were undetectable by λgtll lysogen extract having no cDNA. The results indicated that protein encoded by the cDNA cloned in λ2 has a property of binding to the probe DNA.

⑧ Identification of protein-binding site on the DNA fragment by footprint analysis To a 75 µl of reaction solution containing 10 mM of Tris-HCl (pH 7.5), 50 mM NaCl, one mM DTT, 0.5 mM of EDTA, 2.5 mM of MgCl$_2$, three µg poly(dI-dC)·poly(dI-dC) and 5% glycerol, λ2 lysogen extract containing 16 µg protein (as total protein) and SmaI/HincII probe, prepared from pAFE (HgiAI/BstNI)1 described in ⑤, was mixed and allowed to stand at room temperature for 30 minutes. The probe was labeled with $^{32}$P on only one of the 5' termini. To this mixture, one µl of DNase I (40 ng/µl) was added and caused to react for one minute at room temperature, after which 2.3 µl of 0.5 M EDTA was added to cease the reaction. The reaction mixture was applied to a 5% polyacrylamide gel for gel shift assay, and was subjected to electrophoresis at 11 V/cm until bromophenol blue migrated close to the lower end of the gel.

After removing one glass plate, the gel was wrapped with Saran Wrap (Asahi Chemical Ind. Co., Ltd.), against which an X-ray film was closely placed to make an autoradiogram.

Portions of gel that correspond to the position of DNA bound to protein and that of unbound DNA, determined by the relative mobility of the bands on the autoradiogram, were cut out of the gel. The gel sections were plated separately in 0.5 ml solution composed of 0.5 M ammonium acetate, 0.1% of SDS and one mM of EDTA, and allowed to stand overnight at room temperature to extract the DNA. The mixture was centrifuged (12,000 g, 10 min.) to obtain the supernatant. The gel sections were washed twice with 0.5 ml each of the same elution buffer, after which the washings were mixed with the supernatant (1.3 ml). To this mixture, five µg of yeast transfer RNA (Sigma) was added and the resultant mixture was extracted with a mixture of phenol and chloroform (1:1). To the aqueous phase thus obtained, two volumes of ethanol was added and then allowed to stand for 30 minutes or longer at −70° C. The DNA was then collected by centrifugation (12,000 g, 10 min.), washed once with 70% ethanol and was dried under vacuum. This DNA was dissolved in 10 µl solution composed of 80% formamide, 10 mM of NaOH, one mM of EDTA, 0.1% xylenecyanol and 0.1% bromophenol blue, heated at 90° C. for three minutes, after which 3–4 µl of the solution was applied to an 8% polyacrylamide gel containing seven M urea, which is commonly used to determine nucleotide sequences. The samples were subjected to electrophoresis, together with size markers, which had been prepared from the probe DNA by chemically cleaving at guanine and adenine residues [Method in Enzymology, 65, 499 (1980)].

Figure 6A:
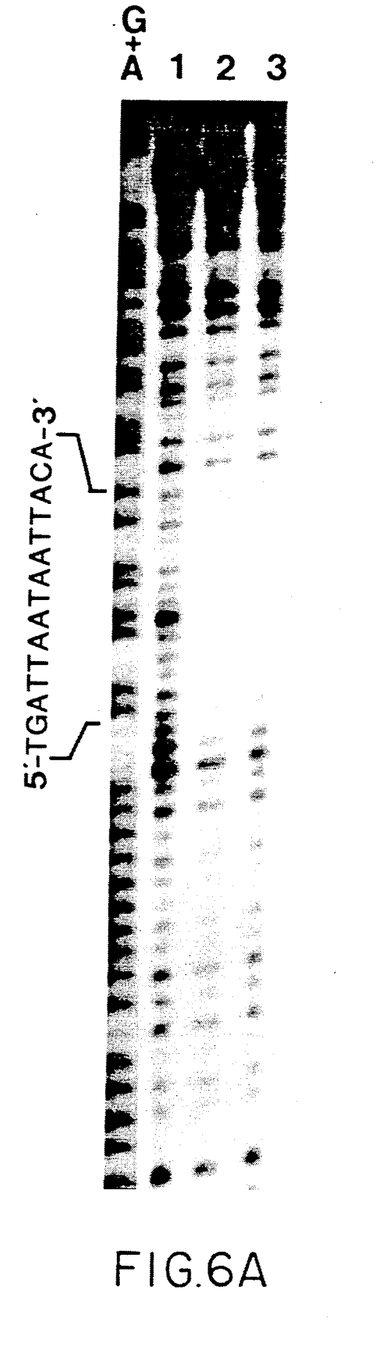
Figure 6B:
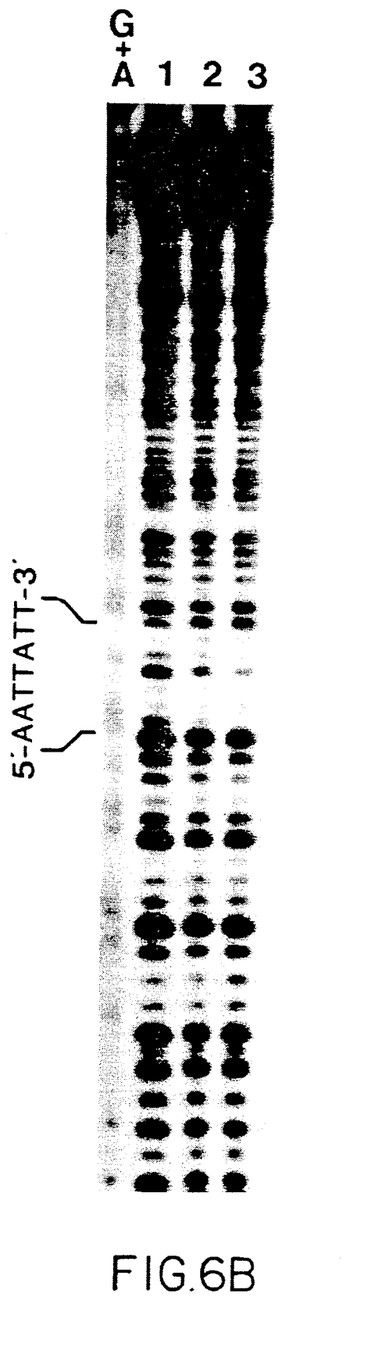
Figure 6C:
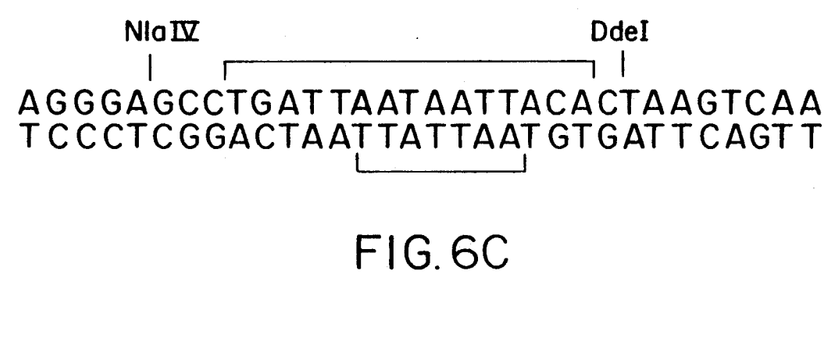

Results of autoradiography performed after electrophoresis are shown in FIG. 6. As shown in the figure, it was indicated that, in DNA bound to the protein encoded by µ2 cDNA, the 15 base pairs containing TTAATAATTA (SEQ ID NO:3) in the middle were protected from cleavage by DNaseI, contrary to the DNA not bound to the protein.

⑨ Nucleotide sequence of cDNA cloned into λ2 phage

DNA of λ2 phage was prepared according to the conventional method [Molecular Cloning, a Laboratory Manual, p. 76 (1982)]. After hydrolysis with EcoRI, an insert DNA fragment was separated by an agarose gel electrophoresis.

Figure 7:
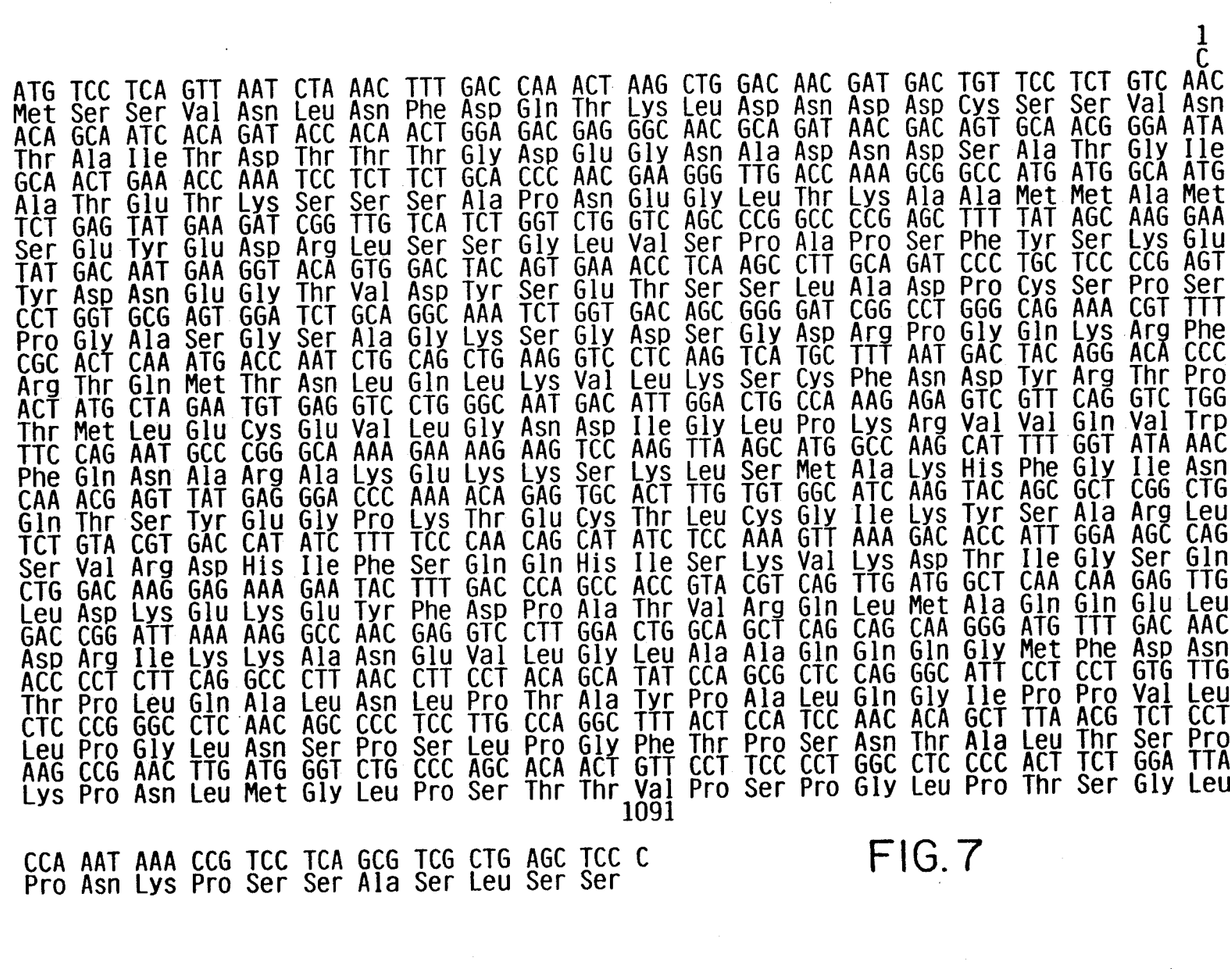
FIG. 7 indicates the nucleotide sequence (SEQ ID NO:1) of the cDNA cloned into λ2, obtained in the example and the amino acid sequence (SEQ ID NO:2) of the protein encoded by it.

FIG. 7 shows the nucleotide sequence of the DNA, determined by dideoxy method [Method in Enzymology, 65, 560 (1980)] and Maxam-Gilbert method [Method in Enzymology, 65, 499 (1989)], and the amino acids sequence of the protein encoded by the DNA.

The fact that the enhancer activity resides on the DNA region to where λ2 cDNA encoded protein binds was confirmed by the following CAT assay.

10 CAT assay

Figure 8:
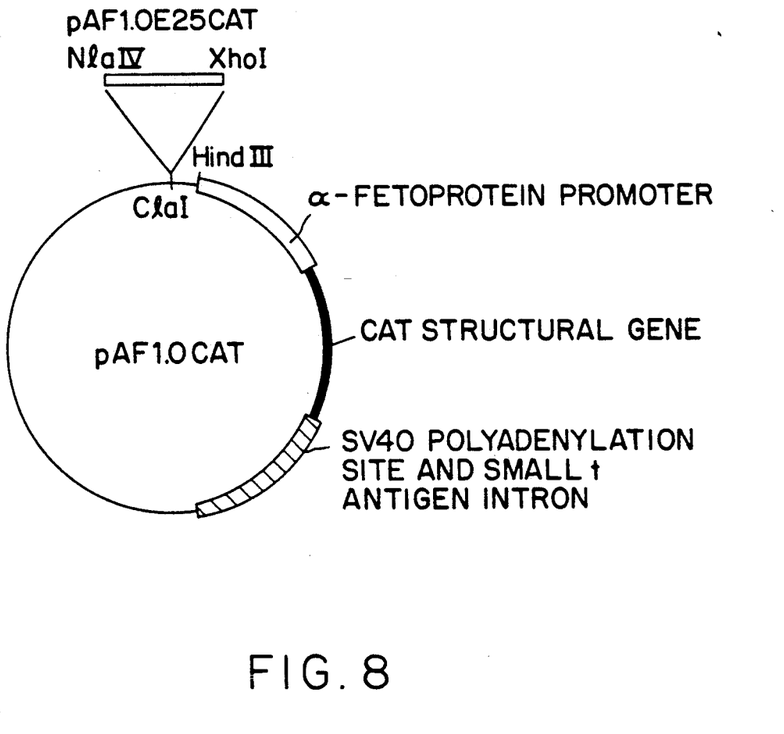
FIG. 8 shows the construction of CAT plasmid pAF1.OE25CAT in the example, which in turn signifies that it was constructed by inserting NlaIV/XhoI fragment (31bp) of the enhancer region into the ClaI site of pAF1.OCAT.

The NlaVI/XhoI fragment isolated from pAFE (HgiAI/XhoI)1, described in ⑤, was inserted into the ClaI site of pAFE1.OCAT, a vector for CAT assay, by blunt-end ligation to obtain pAF1.OE25CAT (see FIG. 8).

The pAF1.OCAT contains one kb DNA of the α-fetoprotein gene promoter region, structural gene for chloramphenicol acetyltransferase of E. coli, and SV40 poly(A) addition signal and t-antigen intron. The vector is used to screen DNA fragment having enhancer activity [J. Biol. Chem., 262, 4812 (1987)]. Transfection of CAT plasmids into HuH-7 cells and CAT assay were performed as follows, based on the known method [Mol. Cell Biol., 2, 1044 (1982)].

About $8 \times 10^6$ cells were grown on a 75 cm² culture flask. To these cells, 20 to 30 μg CAT plasmid DNA was transfected by calcium phosphate method. The cells were incubated for two days in RPMI-1640 culture medium containing 3% lactalbumin hydrolysate, after which the cells were washed with PBS, and scraped off using policeman. Then the cells were collected by low-speed centrifugation (800 rpm, 5 min.), washed once with a solution composed of 40 mM Tris-HCl (pH 7.5), one mM EDTA and 150 mM NaCl, and suspended in 100 μl of 250 mM Tris-HCl (pH 7.5). This suspension was repeatedly frozen and thawed five times to lyse the cells, and centrifuged in an Eppendorf centrifuge at 12,000 rpm for five minutes to obtain a supernatant, which is then heat-treated at 65° C. for 10 minutes. The treated supernatant was again centrifuged at 12,000 rpm for five minutes with the same machine to obtain a supernatant which was used as a cell extract to analyze chloramphenicol acetyltransferase activity.

After determining the protein concentration of the cell extract using the protein assay kit (Biolad), 50–200 μg of protein was used for the following CAT assay.

Figure 9:
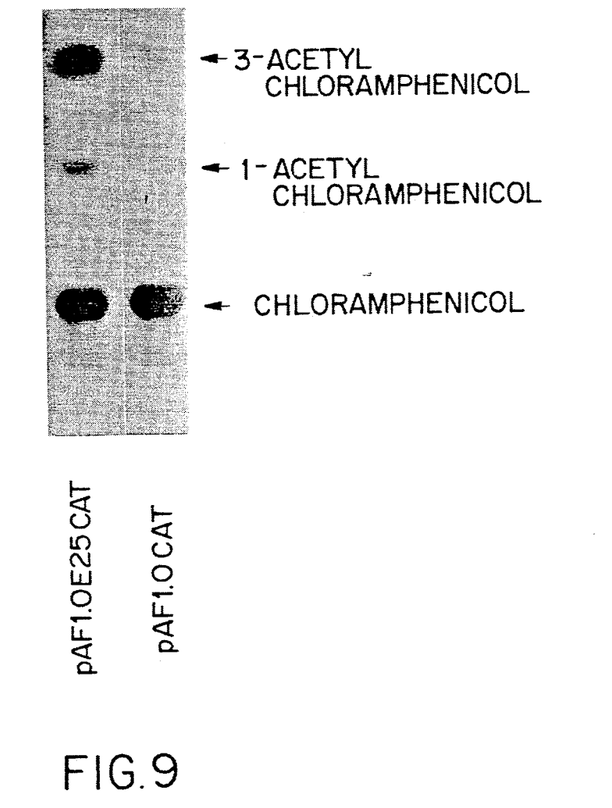
FIG. 9 indicates the CAT assay utilizing cultured human hepatoma cells, HuH-7.

A typical CAT assay reaction mixture, 180 μl, contains 250 mM Tris-HCl (pH 7.5), 0.1 μCi[$^{14}$C] chloramphenicol (Amersham), 0.4 mM acetyl-CoA, and 50–200 μg protein extracted from the cells. This reaction mixture was incubated at 37° C. for 60–180 minutes, after which one ml of ethyl acetate was added to extract chloramphenicol and its acetylated derivatives. The ethyl acetate layer was then separated and dried in vacuo. The residue was redissolved in 20 μl of ethyl acetate, a portion or all of which was applied onto a silica gel plate (Merck). The resultant plate was then developed using chloroform:methanol (96:4, v/v), after which the silica gel plate was dried at room temperature, Saran-wrapped, and subjected to autoradiography. As illustrated in FIG. 9, a greater CAT activity was observed when the experiment was performed with CAT plasmid, pAF1.OE25CAT, which contained the DNA of the enhancer region in the upstream of α-fetroprotein gene, than that of pAF1.OCAT, indicating the presence of an enhancer activity in NlaIV/XhoI fragment.

Industrial Applicability

This DNA is useful in the efficient production of physiologically active proteins in cultured cells, by transfecting (a) an expression vector which produce the enhancer binding protein and (b) an expression vector which contains the enhancer and human α-fetroprotein gene promoter to promote transcription of genes encoding physiologically active proteins.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 1091 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( v i ) ORIGINAL SOURCE:
( A ) ORGANISM: Homo sapiens
( H ) CELL LINE: HuH-7 (human hepatoma)

( x i ) SEQUENCE DESCRIPTION: SEQ ID NO:1:

| | | | | | |
|---|---|---|---|---|---|
| CATGTCCTCA | GTTAATCTAA | ACTTTGACCA | AACTAAGCTG | GACAACGATG | ACTGTTCCTC | 60
| TGTCAACACA | GCAATCACAG | ATACCACAAC | TGGAGACGAG | GGCAACGCAG | ATAACGACAG | 120
| TGCAACGGGA | ATAGCAACTG | AAACCAAATC | CTCTTCTGCA | CCCAACGAAG | GGTTGACCAA | 180
| AGCGGCCATG | ATGGCAATGT | CTGAGTATGA | AGATCGGTTG | TCATCTGGTC | TGGTCAGCCC | 240

-continued

```
GGCCCCGAGC TTTTATAGCA AGGAATATGA CAATGAAGGT ACAGTGGACT ACAGTGAAAC       300
CTCAAGCCTT GCAGATCCCT GCTCCCCGAG TCCTGGTGCG AGTGGATCTG CAGGCAAATC       360
TGGTGACAGC GGGGATCGGC CTGGGCAGAA ACGTTTTCGC ACTCAAATGA CCAATCTGCA       420
GCTGAAGGTC CTCAAGTCAT GCTTTAATGA CTACAGGACA CCCACTATGC TAGAATGTGA       480
GGTCCTGGGC AATGACATTG GACTGCCAAA GAGAGTCGTT CAGGTCTGGT TCCAGAATGC       540
CCGGGCAAAA GAAAAGAAGT CCAAGTTAAG CATGGCCAAG CATTTTGGTA TAAACCAAAC       600
GAGTTATGAG GGACCCAAAA CAGAGTGCAC TTTGTGTGGC ATCAAGTACA GCGCTCGGCT       660
GTCTGTACGT GACCATATCT TTTCCCAACA GCATATCTCC AAAGTTAAAG ACACCATTGG       720
AAGCCAGCTG GACAAGGAGA AAGAATACTT TGACCCAGCC ACCGTACGTC AGTTGATGGC       780
TCAACAAGAG TTGGACCGGA TTAAAAAGGC CAACGAGGTC CTTGGACTGG CAGCTCAGCA       840
GCAAGGGATG TTTGACAACA CCCCTCTTCA GGCCCTTAAC CTTCCTACAG CATATCCAGC       900
GCTCCAGGGC ATTCCTCCTG TGTTGCTCCC GGGCCTCAAC AGCCCCTCCT TGCCAGGCTT       960
TACTCCATCC AACACAGCTT TAACGTCTCC TAAGCCGAAC TTGATGGGTC TGCCCAGCAC      1020
AACTGTTCCT TCCCCTGGCC TCCCCACTTC TGGATTACCA AATAAACCGT CCTCAGCGTC      1080
GCTGAGCTCC C                                                          1091
```

(2) INFORMATION FOR SEQ ID NO:2:

(i) SEQUENCE CHARACTERISTICS:
(A) LENGTH: 363 amino acids
(B) TYPE: amino acid
(C) STRANDEDNESS: double
(D) TOPOLOGY: linear (ii) MOLECULE TYPE: protein (vi) ORIGINAL SOURCE:
(A) ORGANISM: Homo sapiens
(H) CELL LINE: HuH-7 (human hepatoma)

(xi) SEQUENCE DESCRIPTION: SEQ ID NO:2:

```
Met Ser Ser Val Asn Leu Asn Phe Asp Gln Thr Lys Leu Asp Asn Asp
  1               5                  10                  15
Asp Cys Ser Ser Val Asn Thr Ala Ile Thr Asp Thr Thr Thr Gly Asp
             20                  25                  30
Glu Gly Asn Ala Asp Asn Asp Ser Ala Thr Gly Ile Ala Thr Glu Thr
         35                  40                  45
Lys Ser Ser Ser Ala Pro Asn Glu Gly Leu Thr Lys Ala Ala Met Met
     50                  55                  60
Ala Met Ser Glu Tyr Glu Asp Arg Leu Ser Ser Gly Leu Val Ser Pro
 65                  70                  75                  80
Ala Pro Ser Phe Tyr Ser Lys Glu Tyr Asp Asn Glu Gly Thr Val Asp
                 85                  90                  95
Tyr Ser Glu Thr Ser Ser Leu Ala Asp Pro Cys Ser Pro Ser Pro Gly
                100                 105                 110
Ala Ser Gly Ser Ala Gly Lys Ser Gly Asp Ser Gly Asp Arg Pro Gly
            115                 120                 125
Gln Lys Arg Phe Arg Thr Gln Met Thr Asn Leu Gln Leu Lys Val Leu
        130                 135                 140
Lys Ser Cys Phe Asn Asp Tyr Arg Thr Pro Thr Met Leu Glu Cys Glu
145                 150                 155                 160
Val Leu Gly Asn Asp Ile Gly Leu Pro Lys Arg Val Val Gln Val Trp
                165                 170                 175
Phe Gln Asn Ala Arg Ala Lys Glu Lys Lys Ser Lys Leu Ser Met Ala
            180                 185                 190
```

|   |   |   |   |   |   |   |   |   |   |   |   |   |   |   |
|---|---|---|---|---|---|---|---|---|---|---|---|---|---|---|
| Lys | His | Phe 195 | Gly | Ile | Asn | Gln | Thr 200 | Ser | Tyr | Glu | Gly | Pro 205 | Lys | Thr | Glu |
| Cys | Thr 210 | Leu | Cys | Gly | Ile | Lys 215 | Tyr | Ser | Ala | Arg | Leu 220 | Ser | Val | Arg | Asp |
| His 225 | Ile | Phe | Ser | Gln | Gln 230 | His | Ile | Ser | Lys | Val 235 | Lys | Asp | Thr | Ile | Gly 240 |
| Ser | Gln | Leu | Asp | Lys 245 | Glu | Lys | Glu | Tyr | Phe 250 | Asp | Pro | Ala | Thr | Val 255 | Arg |
| Gln | Leu | Met | Ala 260 | Gln | Gln | Glu | Leu | Asp 265 | Arg | Ile | Lys | Lys | Ala 270 | Asn | Glu |
| Val | Leu | Gly 275 | Leu | Ala | Ala | Gln | Gln 280 | Gln | Gly | Met | Phe | Asp 285 | Asn | Thr | Pro |
| Leu | Gln 290 | Ala | Leu | Asn | Leu | Pro 295 | Thr | Ala | Tyr | Pro | Ala 300 | Leu | Gln | Gly | Ile |
| Pro 305 | Pro | Val | Leu | Leu | Pro 310 | Gly | Leu | Asn | Ser | Pro 315 | Ser | Leu | Pro | Gly | Phe 320 |
| Thr | Pro | Ser | Asn | Thr 325 | Ala | Leu | Thr | Ser | Pro 330 | Lys | Pro | Asn | Leu | Met 335 | Gly |
| Leu | Pro | Ser | Thr 340 | Thr | Val | Pro | Ser | Pro 345 | Gly | Leu | Pro | Thr | Ser 350 | Gly | Leu |
| Pro | Asn | Lys 355 | Pro | Ser | Ser | Ala | Ser 360 | Leu | Ser | Ser |

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear     ( i i ) MOLECULE TYPE: cDNA to mRNA     ( i i i ) HYPOTHETICAL: NO     ( v i ) ORIGINAL SOURCE:
        ( A ) ORGANISM: Homo sapiens
        ( H ) CELL LINE: HuH-7 (human hepatoma)

( i x ) FEATURE:
        ( A ) NAME/KEY: enhancer
        ( B ) LOCATION: 1..10

( x i ) SEQUENCE DESCRIPTION: SEQ ID NO:3:

TTAATAATTA                                                              10

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Bacteriophage lambda
        ( B ) STRAIN: lambda gt11

( v i i i ) POSITION IN GENOME:
        ( A ) CHROMOSOME/SEGMENT: lacZ gene EcoRI site     ( x i ) SEQUENCE DESCRIPTION: SEQ ID NO:4:

GCGGAATTCC AG                                               12

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: double
        (D) TOPOLOGY: linear     (ii) MOLECULE TYPE: peptide     (vi) ORIGINAL SOURCE:
        (A) ORGANISM: Bacteriophage lambda
        (B) STRAIN: lambda gt11

(viii) POSITION IN GENOME:
        (A) CHROMOSOME/SEGMENT: lacZ gene EcoRI site     (xi) SEQUENCE DESCRIPTION: SEQ ID NO:5:

Ala Glu Phe Gln
1

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: double
        (D) TOPOLOGY: linear     (ii) MOLECULE TYPE: cDNA to mRNA     (vi) ORIGINAL SOURCE:
        (A) ORGANISM: Homo sapiens
        (H) CELL LINE: HuH-7 (human hepatoma)

(xi) SEQUENCE DESCRIPTION: SEQ ID NO:6:

TGATTAATAA TTACA        15

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: double
        (D) TOPOLOGY: linear     (ii) MOLECULE TYPE: cDNA to mRNA     (vi) ORIGINAL SOURCE:
        (A) ORGANISM: Homo sapiens
        (H) CELL LINE: HuH-7 (human hepatoma)

(xi) SEQUENCE DESCRIPTION: SEQ ID NO:7:

AGGGAGCCTG ATTAATAATT ACACTAAGTC AA        32

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: double
        (D) TOPOLOGY: linear     (ii) MOLECULE TYPE: cDNA     (vi) ORIGINAL SOURCE:
        (A) ORGANISM: Homo sapiens
        (H) CELL LINE: HuH-7 (human hepatoma)

(xi) SEQUENCE DESCRIPTION: SEQ ID NO:8:

TTGACTTAGT GTAATTATTA ATCAGGCTCC CT        32

We claim:

1. An isolated DNA sequence for coding for a protein having the amino acid sequence SEQ ID NO:2.

2. A DNA of claim 1, wherein said protein-coding DNA comprises the sequence SEQ ID NO:1.

3. An isolated protein having the amino acid sequence SEQ ID NO:2.

* * * * *